(12) United States Patent
Harty

(10) Patent No.: US 6,405,389 B1
(45) Date of Patent: Jun. 18, 2002

(54) COMPACT PORTABLE CONTAMINATION CONTROL DEVICE

(76) Inventor: Robert D. Harty, 13124 Regan Rd., Mokena, IL (US) 60448

( * ) Notice: Subject to any disclaimer, the term of this patent is extended or adjusted under 35 U.S.C. 154(b) by 0 days.

(21) Appl. No.: 09/457,422

(22) Filed: Dec. 7, 1999

Related U.S. Application Data

(63) Continuation-in-part of application No. 08/960,265, filed on Oct. 29, 1997, now abandoned.

(51) Int. Cl.[7] ............................................... A47K 3/022
(52) U.S. Cl. ............................................................ 4/621
(58) Field of Search ............................................ 4/621

(56) References Cited

U.S. PATENT DOCUMENTS

| | | | |
|---|---|---|---|
| 3,083,376 A | * | 4/1963 | Johns .............................. 4/621 |
| 3,513,488 A | * | 5/1970 | Oring et al. ................. 4/456 X |
| 5,107,857 A | * | 4/1992 | Linnemann et al. ........ 4/587 X |
| 5,568,817 A | * | 10/1996 | Harty ......................... 4/458 X |

* cited by examiner

Primary Examiner—Robert M. Fetsuga
(74) Attorney, Agent, or Firm—Cherskov & Flaynik

(57) ABSTRACT

A versatile, compact, rapidly deployable and easily disposable contamination device that can accommodate various regions of the human body in isolation is provided. The device is deployable in a few seconds; isolates a patient's body region; accommodates any of the extremities of the human body, as well as the head and limbs, while minimizing the patient's discomfort; allows for the drainage and storage of contaminants and body fluids; and is easily disposable as a whole in a container provided for that purpose. Portions of the device are re-usable while other portions of the device are utilized to store contaminating fluid.

13 Claims, 7 Drawing Sheets

COMPACT PORTABLE CONTAMINATION CONTROL DEVICE

This is a Continuation-In-Part of application Ser. No. 08/960,265, filed Oct. 29, 1997 abandoned.

BACKGROUND OF THE INVENTION

1. Field of the Invention

This invention relates to contamination control devices and more specifically to portable, folding, disposable devices intended to control fluid flow during decontamination or medical treatment of an isolated region of a patient's body.

2. Background of the Invention

Injuries or illnesses affecting a specific region of a patient's body present special problems to medical and emergency rescue personnel. These problems include control and containment of the blood or other body fluids flowing as a result of an injury or a surgical procedure.

Decontamination of patient parts from hazardous, biological, chemical, or radioactive agents also poses fluid handling concerns. In these cases, decontamination of the effected area also requires that the rest of the patient be shielded from contamination.

In addition to the above, very often treatment has to be provided on an emergency basis at an accident or disaster location and to a very large number of individuals. In all cases one must dispose of the contaminants, body fluids, contaminated clean-up materials and containers in a safe and expeditious manner. Prior art methods for facilitating the medical treatment of isolated regions of the human body and for containing contaminants and effluents have proven to be unsatisfactory in many respects. Several patents have disclosed devices where the whole body is immersed in the decontamination device so that contaminants washed away from the primary contamination site come into contact with areas of the body that were heretofore uncontaminated. See U.S. Pat. Nos. 3,112,498, 4,305,165, 4,713,850, 4,960,136 and U.S. Pat. No. 5,426,795, the last of which was issued to the Applicant. Generally, these devices have several disadvantages: they require a long time to deploy, are difficult to dispose of in large quantities, and are relatively expensive. As such, disaster preparedness officials have found it impracticable to store a sufficient quantity of such devices on first-aid vehicles or at triage stations in anticipation of their possible use. Consequently when the need suddenly arises, not enough devices are available.

Also, whole body contamination is somewhat unusual. More usually, only the head or an extremity needs to be treated. As such, the use of a full body decontamination tub or basin to treat a small body region is wasteful.

Other devices can be characterized as surgical drapes. See U.S. Pat. Nos. 3,921,627 4,890,628, 5,107,859 5,143,091, and 5,161,544, These are intended for use with a specific region of the body, the knee for instance, and they are provided with some means for the storage of effluents. On the other hand, these devices are so specialized in their use that disaster preparedness officials find it unpracticable to supply adequate assortments to ambulances or to dispersed stations. Moreover, because they cannot accommodate sufficient quantities of fluid these devices cannot be readily used for decontamination. Also, these devices do not afford simultaneous, unimpeded access to all areas of an effected body region without the necessity of clamps or folds.

A need exists in the art for a device that controls fluid run-off resulting from decontamination and treatment of isolated regions of the human body and for other similar activities. The device should be deployed rapidly, and should also serve to contain hazardous fluids for subsequent disposal.

SUMMARY OF THE INVENTION

It is an object of the present invention to provide a decontamination and body-fluid containment device that overcomes many of the disadvantages in the prior art.

Another object of the present invention to provide a device to decontaminate an isolated body region. A feature of the present invention is that it is compact. An advantage of the present invention is that it isolates the rest of a patient's body from the contaminant as the contaminant is removed from the primary effected site.

It is a further object of the present invention to provide a decontamination device such that an isolated body region undergoing treatment may be supported so as to minimize patient discomfort. A feature of the present invention is that it provides means to minimize the pressure exerted on the body region. An advantage of the present invention is that the patient's body region may rest comfortably and securely while under treatment. Another advantage is that the support means is contoured so as to prevent fluid leakage between the body region and the support means.

Yet a further object of the present invention is to provide a decontamination device where treating personnel have unimpeded access to an isolated body region undergoing treatment. A feature of the present invention is that it allows the body region to be positioned well above the treatment device. An advantage of the present invention is that the body region may be treated in its entirety without moving the patient.

Another object of the present invention is to provide a decontamination device with which a variety of isolated body regions may be decontaminated. A feature of the present invention is that it is adaptable to any body extremity and to a variety of other body regions. An advantage of the present invention is that identical embodiments thereof can be used to treat a wide variety of injuries or diseases. Another advantage is that the invention has many surgical- and emergency-department uses in a medical setting, wherein eye or ear irrigation is common, and where the treatment for head-, hand-, and extremity-trauma is common place. The device could also be utilized as a surgical or suture tray, with the tray to optionally contain an absorbent material as in inside bottom liner.

Still another object of the present invention is to provide a decontamination device that allows substantial quantities of contaminants and other effluents to be drained away. A feature of the present invention is that it provides drainage means together with a receptacle for the liquid drained away. An advantage of the present invention is that contamination of the surroundings is minimized. These advantages allows the device, when constructed with pliable frame members, to be used as a bed-pan.

It is a further object of the present invention to provide a decontamination device that is of minimal bulk. A feature of the present invention is that it is collapsible. An advantage of the present invention is that the device can be easily shipped and stored prior to use. Another advantage is that the device can be used as a hazardous fluid storage container after it's primary function, of catching the hazardous material, has been utilized.

Yet a further object of the present invention to provide a decontamination device that can be deployed rapidly. A feature of the present invention is that it requires minimal or no assembly. An advantage of the present invention is that it can be used to immediately contain fluid which poses a sudden potential for spreading.

Another object of the present invention to provide a decontamination device which is of minimal cost. A feature of the present invention is that it comprises a few compact parts that are readily fabricated with common materials. An advantage of the present invention is that disaster preparedness officials may store a sufficient supply of decontamination devices at dispersed sites where such devices may someday be needed.

Yet another object of the present invention is to provide a semi-reusable decontamination device and fluid catch basin. A feature of the device is that a frame is isolated from contaminating fluid by a membrane. An advantage of the device is that the membrane can be discarded or used to store the contaminating fluid and the frame can be reused in subsequent decontamination instances.

Briefly, the invention provides a device to isolate a patient's body region and to contain fluid emanating from the region comprising a frame; a membrane attached to said frame to define a basin; and a means provided on said frame to receive the body region.

Also provided is a device for isolating a site and capturing fluid associated with the site, comprising a frame; a membrane attached to said frame to define a basin; and a means for enabling the basin to encapsulate the site.

The invention also provides for a collapsible basin comprising a foldable, compliant frame; and membrane received by said frame to form a basin.

Also provided is a device to isolate a patient's body region and to contain fluid emanating from the region comprising a reversibly deformable frame; and a membrane attached to said frame to define a basin and to isolate the frame from the basin.

DETAILED DESCRIPTION OF THE INVENTION

The present invention provides a versatile, compact, low-cost, rapidly deployable and easily disposable contamination device that can accommodate various regions of the human body in isolation. The device is deployable in a few seconds (as short as five seconds), accommodates any of the extremities of the human body, as well as the head and limbs, while minimizing the patient's discomfort, allows for the drainage and storage of contaminants and body fluids, and is easily disposable as a whole in a container provided for that purpose.

Figure 1:
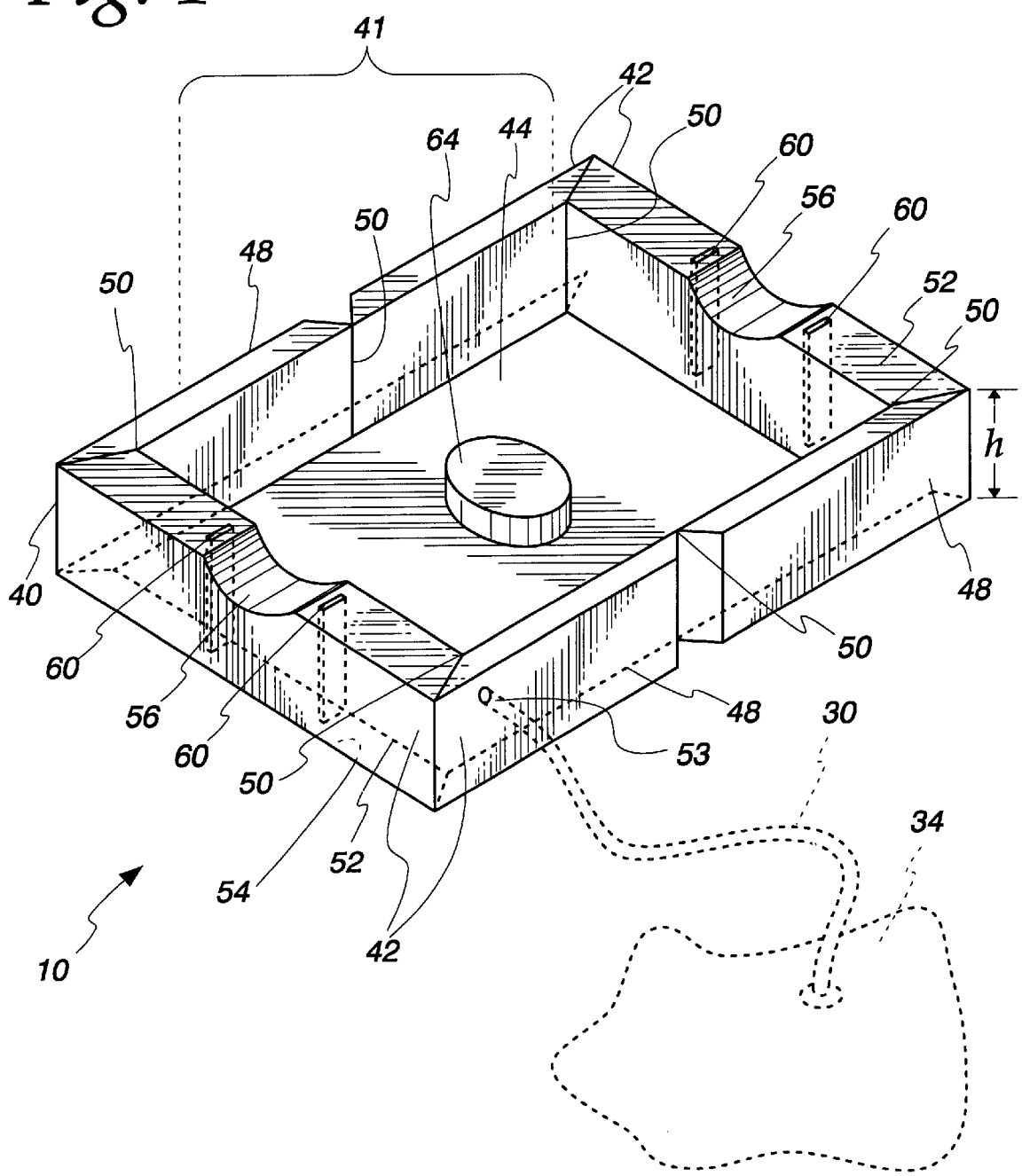
FIG. 1 is an elevated perspective view of an exemplary fluid containment device illustrating the present invention.

A myriad of different embodiments and uses for the invention can be envisioned. One exemplary embodiment of the invented device is depicted in FIG. 1 as numeral 10. As depicted in FIG. 1, the device 10 comprises a frame 40 to which a liner 44 is attached to a depending edge 54 of the frame 40 to form a basin 41. The basin 41 is large enough to contain fluid emanating from a treated body part or large enough to receive a backboard used in veterinary science for the transport and treatment of animals. The basin can also contain means 64 positioned therein, such as a support cushion, for supporting the body region.

The frame 40 comprises a plurality of generally elongated members 42 having a height h sufficient to enable the basin to hold any fluid being evacuated from an effected body region. While the illustrated embodiment shows the heights h the same for all of the elongated members 42, the heights of opposing sides 48 or 52 of the basin can vary to facilitate draining over the top of a lower opposing side. To facilitate drainage in this scenario, the top of the lower side can be additionally formed to direct fluid flow over one region of the top of the lower side. Typically, the frame 40 is rectangular in shape.

Figure 4:
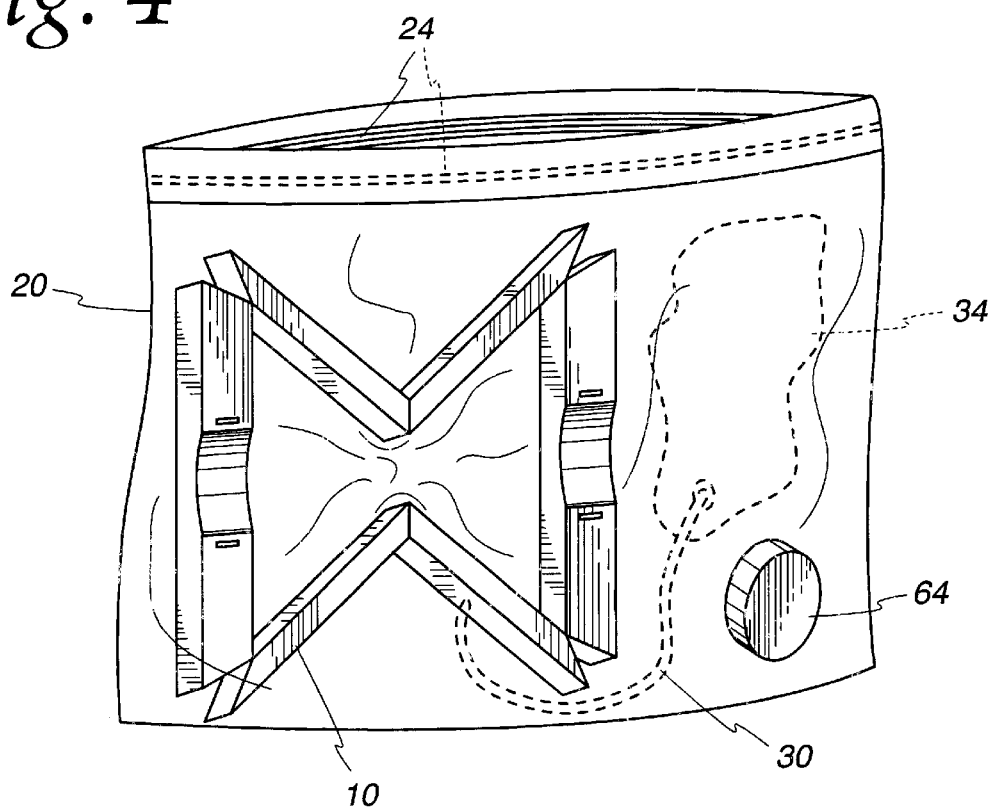
FIG. 4 is a plan view of the present device when supplied in a collapsed form inside a container.

Optionally, means 50 for flexibly joining constituents of the elongated members 48 or 52 to each other are employed so that the device can be stored in a collapsed or folded state, as depicted in FIG. 4. Alternatively, and as taught in U.S. Pat. No. 5,568,817, awarded to applicant and incorporated herein by reference, the elongated members can be perforated 75 to promote folding at defined points along the elongated members to facilitate packing and unpacking (or deployment) of the device.

Still another modification of the invention is where the frame is comprised of a reversibly deformable material so as to enable the basin 41 to encircle or otherwise encapsulate a fluid emanating region. This embodiment would be particularly helpful to minimize exposure of an injured body region (such as in instances of a protruding fracture) to the environment. In this situation, the device could be partially wrapped around the effected site to both minimize exposure and to capture fluid emanating from the wound site during transport. Another use of the device having reversibly deformable frame members is as a wrap-around containment means for leaking pipes, vessels and other ruptured containers.

The frame members can also be comprised of a pliable material. This would allow a bed-ridden patient to use the device as a bed pan without the extremely uncomfortable, pressure-point characteristics of typical bed-pan configurations.

When fully deployed, a device assumes a form to minimize bulkiness. Exemplary forms include, but are not limited to, a rectangle, square, half sphere, or oval. FIG. 1 also shows an optional drainage conduit 30 and a receptacle for the drainage 34. The receptacle can be removably attached to the drainage conduit. In this instance, the drainage conduit 30 may interface a region of an elongated member 42, which region defines a transverse aperture 53 through the elongated member. A means for providing a leak-proof connection between the aperture 53 and the conduit 30 is provided, which is disclosed in U.S. Pat. No. 5,568,817. Briefly, a threaded nipple adapted to be received by the aperture 53 can be utilized and mated with a complementary female fitting located at a proximal end of the conduit 30, the distal end of the conduit 30 being attached to the drainage receptacle.

As shown in FIG. 1, upwardly directed edges of the frame 40 are each provided with a means for positioning a body part. An exemplary positioning means is depicted as niches wherein two opposing sides 52 of the frame are adapted to accommodate the transverse positioning of the neck, a limb, or other body region. The niches allow a marked reduction of the pressure exerted on the body region. When resting in the niches, the body region under treatment will not come into contact with the contaminated liquid or other effluents captured by the basin. In effect, transverse positioning of the body part suspends the body part over the draining fluid, thereby isolating the once-contaminated, now decontaminated part from the fluid. The "mating" of the body part with the niches also forms a seal to prevent fluid leakage between the body part and the niche thereby isolating uncontaminated regions of the rest of the patient.

On each side of the niches 56 slots 60 are provided to accommodate optional flexible straps (not shown) that allow the body region to be more firmly secured when circumstances require it.

Figure 2:
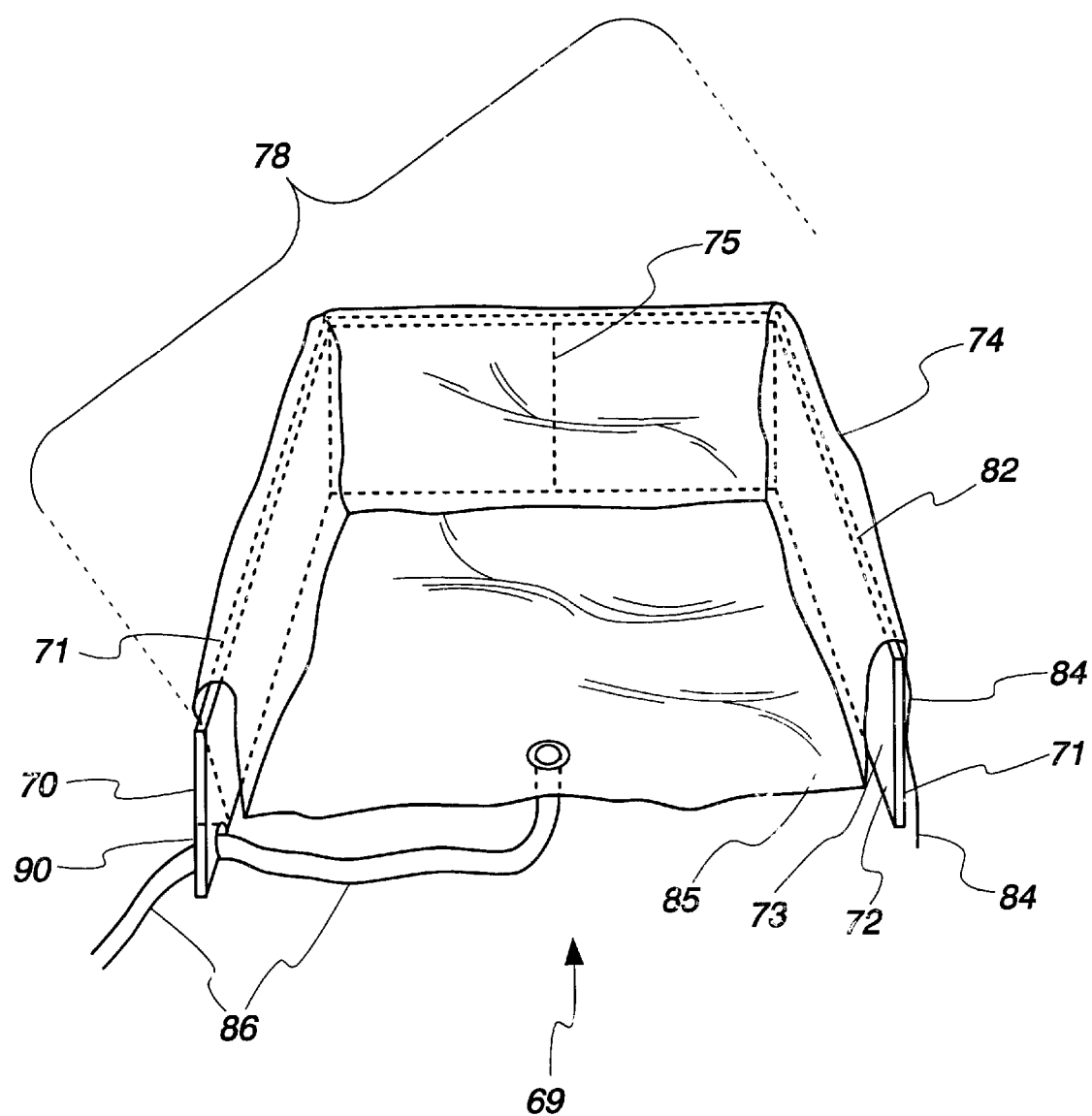
FIG. 2 is an elevated cut-away view of an alternative embodiment of the device, in accordance with the features of the present invention.

FIG. 2 shows a cut-away view of another embodiment designated as numeral 69, of the device. Generally, this embodiment is similar to the applicant's embodiment taught in U.S. Pat. No. 5,568,817, and incorporated herein by reference. A foldable frame 70 of the type taught in the '817 patent is supplied. A flexible membrane 74 is draped over the frame 70 so as to define a basin 78. The membrane may be attached to the frame 70 at an upwardly directed rim 82 of the frame 70 either permanently (i.e. through RF, Welding or adhesive) or reversibly attached, as by hook-and-pile type fasteners (such as Velcro®), or snap-fit assembly. In the alternative, the membrane is allowed to hang over the outer sides 71 of the frame 70. In this case, the pressure of the patient's body region resting on the frame will hold the membrane in place. In yet another alternative embodiment, a depending end 84 of the draped membrane 74 is attached to the outer sides 71 of the frame 70, the depending edge 72 of the frame 70, the inner surface 73 of the frame 70, or tucked between the inner surface 73 of the frame 70 and the membrane 74.

In a preferred embodiment, the depending end 84 of the membrane 74 is reversibly or irreversibly joined (via a means for joining such as, but not limited to, RF welding, adhesive, hook-and-pile type fasteners, or snaps) to an outside surface 85 of the membrane 74

This configuration can completely encapsulate and isolate the frame 70 structure from the environment.

A means for draining fluid from this alternative embodiment can be supplied. As shown, a drainage conduit 86 is attached (through RF welding, adhesive or other attachment means) to the membrane 74. A notch 90 provided in the wall of the frame allows the conduit to carry fluid away from the basin 78. The notch also allows for the device to sit level on its resting surface by nesting the conduit so that the conduit surface remains flush with the depending edge 72 of the frame.

It must be noted that in the embodiment where the membrane is not bonded to the frame, the same frame can be used to serve an arbitrary number of patients when a different membrane is used with each patient. This last embodiment allows the treatment of a large number of patients at a very low cost and with materials of relatively small bulk.

Construction Detail

While the present invention provides for the membrane to be removably attached to the frame, certain embodiments have the membrane bonded to the frame, or integrally molded to the frame. Other embodiments require that the membrane be bonded to itself. Methods for such bonding include, but are not limited to, RF welding, joining with an adhesive, and thermal treatment. Materials that are not readily amenable to such bonding may be used for the frame provided they are clad with flexible materials such as those recommended for the membranes. Then one may bond the cladding to the membrane. Cladding of the frame members would allow the use of a wider range of materials for the frame, including but not limited to styrofoam, foam rubber, ethyl vinyl acetate, or other compliant or hand-moldable materials that would provide a more comfortable niche for the patient. Also, the drainage means 30 may be attached to the device by the methods described above.

Under certain circumstances one may require that the basin comprised in the device 10 drain continuously into a large reservoir. This can be accomplished most easily by tilting the device to allow liquid to flow over one of the frame members 48 into the larger reservoir. In the alternative, one may make one the frame members 48 lower than the other and thus allow liquid to flow out of the device. More typically, fluid would drain from the bottom or near the bottom edge of one of the upwardly directed sides of the basin through the drainage means 30.

More typical construction of the device includes the fabrication of the frame member that is essentially one continuous piece of elongated substrate having a first end and a second end. The substrate is folded or otherwise configured into the desired basin periphery shape. The first ends and second ends are subsequently joined. Then, the membrane material 74 is applied to the frame 70 and secured in various configurations as discussed above.

Figure 3:
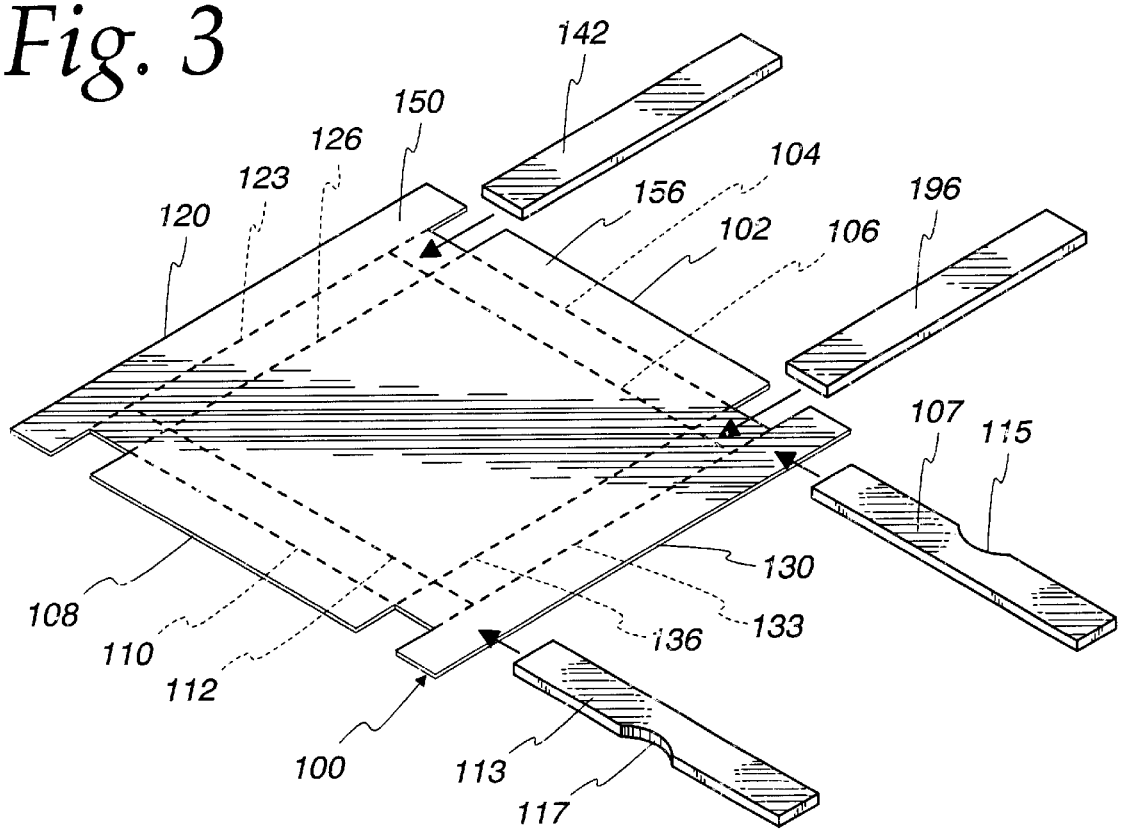
FIG. 3 is an exploded perspective view of an alternate embodiment of the present invention as well as a method for manufacturing the present invention.

FIG. 3 depicts an alternative embodiment as well as a possible means for fabrication of the invention. A sheet of substrate 100 which represents the membrane is cut as shown. Edge 102 is folded up (out of the plane of the paper) at crease 104 and RF welded along line 106. Then rigid member 107 is inserted into the sleeve thus formed with one end positioned at line 126 and the other at line 136. The same operation is repeated with edge 108, folded at crease 110 and RF welded at line 112. Then rigid member 113 is inserted in the sleeve thus formed. Note that members 107 and 113 have niches 115 and 117 to accommodate the body region to be treated. Similarly edge 120 is folded at crease 123 and welded at line 126 and edge 130 is folded at crease 133 and welded at line 136, with rigid members 142 and 146 inserted in the sleeves thus formed. Finally the underside of flap 150 is 30 placed against section 156 and RF welded thereto. The same process is repeated at the other three corners. The net result of this operation is a basin the bottom of which is formed by lines 106, 136, 112 and 126 and the rim by creases 104, 133, 110, and 123.

The operation described above is to be performed at a plant but it can easily be modified for field assembly: the four peripheral sleeves would be RF welded at the plant but the rigid members would be inserted on location. Hook-andpile patches (such as Velcro®) or snap fasteners could be provided at flap 150 and location 156 (as well as at the corresponding locations at the other three corners) so that these regions can be joined thereby. Any of the membrane materials cited in conjunction with the previous embodiment can be used in this embodiment. The rigid members in this embodiment may consist of compliant or pliable materials such as foam rubber, Styrofoam, etc as well as any other rigid material. This embodiment has the advantage of minimizing the weight and bulk of the device and of allowing a wide choice of frame materials.

FIG. 4 depicts the device in a collapsed or folded up state I; and contained in a plastic bag 20. The bag 20 is provided for storage of the device prior to its use and for disposal thereof once it has been used. The bag 20 has a resealable opening 24. The opening 24 is provided with such liquid-proof resealing means as an adhesive or reversibly deformable tongue-and-groove type configurations such as ZipLoc™ closures. The bag 20 is spacious enough to accommodate the device 10 itself, the support cushion 64, as well as optionally provided draining means 30 and collapsible drainage receptacle 34 together with whatever other contaminated materials are to be disposed of once treatment is completed. The provision of the resealable bag 20 is of special utility when patients are treated at accident or disaster sites or when fluids to be contained are pathogenic radioactive, or otherwise hazardous. The materials suitable for the membranes 44 and 50 described above can be used for the plastic bag 20.

Alternatively, the depending edge 84 of the flexible membrane 74 of the device as depicted in FIG. 2 contains means for reversibly attaching opposing edges of the membrane to each other. This allows for the membrane to be converted into a fluid-holding pouch or pod, with the pouch serving as a fluid container for transport, later storage or content analysis. Alternatively, the entire filled-pouch can be disposed via burial, incineration, or other allowable means. Exemplary attaching means includes, but are not limited to hook-and-pile fasteners, male/female snap fit assemblies, or tongue-and-groove type configurations such as Zip-Loc™ mating surfaces.

A preferred embodiment of the containment device incorporates a liner to isolate the frame from any fluids contained by the device. Generally, the liner is form-fitted and optionally removably attached to the frame. This form-fitting interaction also prevents the frame from collapsing. As such, the liner is installed on a fully deployed frame, and serves to encapsulate substantially all of the frame.

Figures 5A, 5B, 5C:
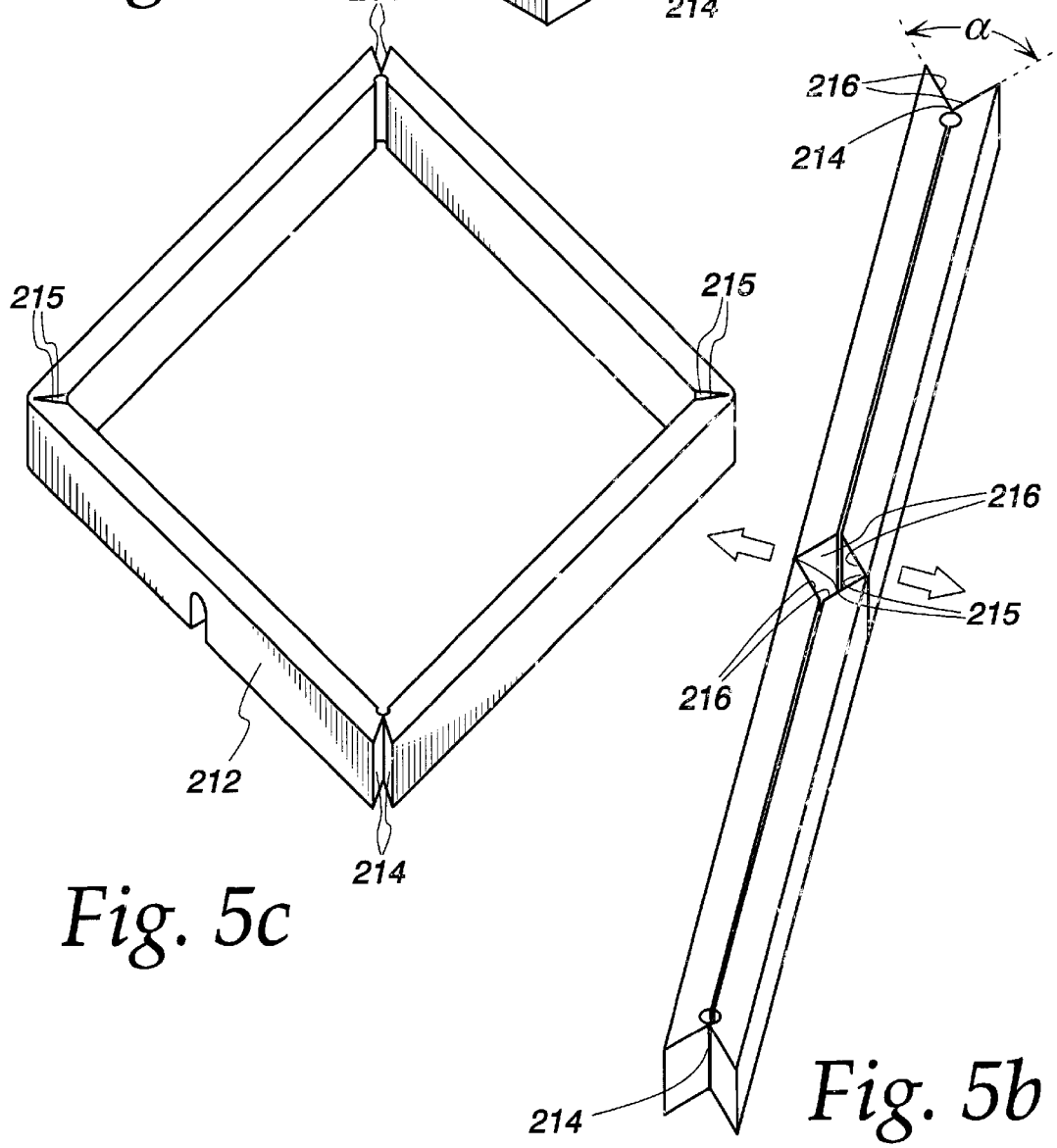
FIG. 5A is an elevated perspective view of an exemplary frame in a deployed state, for use in accordance with features of the present invention.
FIG. 5B is an elevated perspective view of the exemplary frame, but in a collapsed state, in accordance with features of the present invention.
FIG. 5C is an elevated perspective view of the frame in a partially deployed configuration.

FIGS. 5A and 5B are plan views of a fully deployed frame 212 and a fully collapsed frame 212, respectively, which are incorporated in the preferred embodiment. The frame comprises diametrically opposite corner pairs 214 and 215. The collapsed frame (FIG. 5B) is deployed when a force is applied to it in the direction of the arrows. Generally, the frame is comprised of a reversibly deformable material, such as closed cell foam, also known as cellular plastic. Exemplary closed cell foams are available from a myriad of commercial sources, including, but not limited to, Adams Foam, of Chicago, Ill.

As can be noted in FIG. 5B, each corner of the frame 212 defines a pair of opposing surfaces 216, situated at an angle a to each other to facilitate full deployment of the frame to its desired shape. Upon deployment, each corner effects a mitered configuration. In the case of a square frame, the two opposing surfaces of each corner are situated at a 90 degree angle from each other. The mitered corners also allow for collapsing the frame along an axis defined by two points located at diametrically opposed corners 214.

As depicted in FIG. 5B, diametrically opposed corners 214 are configured so that the opposed surfaces 216 comprising each corner 214 face outwardly and in an axial direction when the frame 212 is collapsed. Conversely, a pair of diametrically opposed corners 215 are configured so that the opposed surfaces 216 of one corner face medially when the frame is collapsed, and in close proximity to the opposed surfaces defining the other corner.

Figure 6:
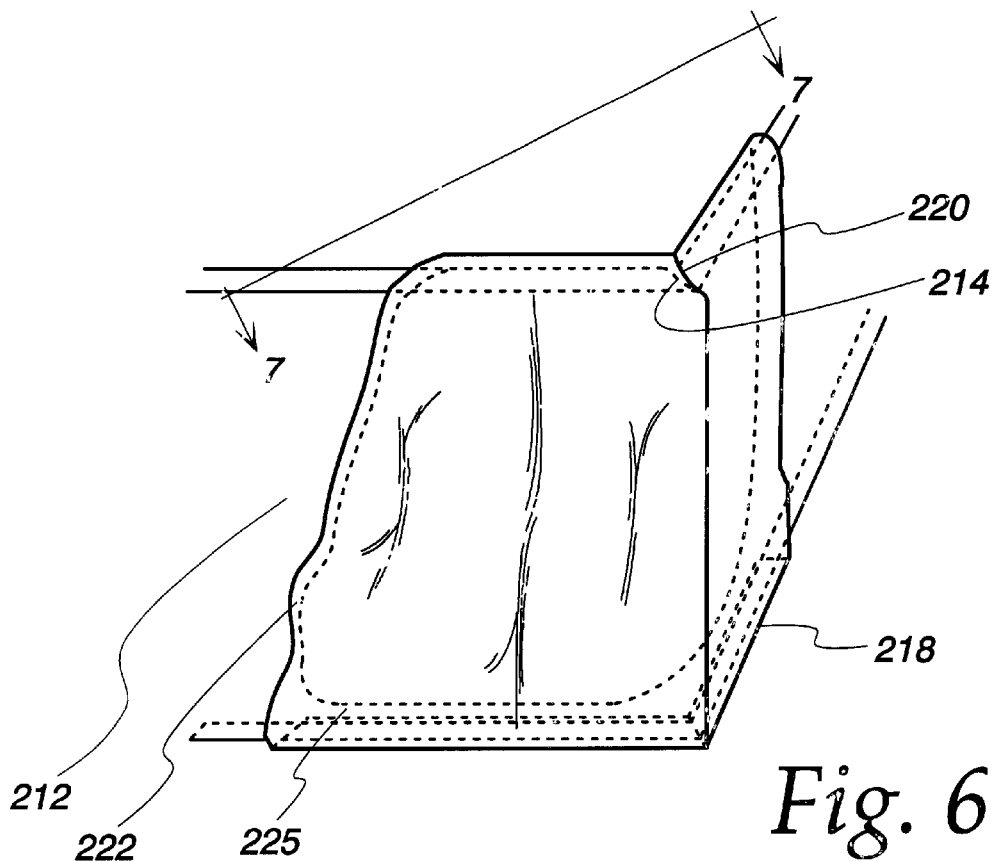
FIG. 6 is a section view of a corner of the frame with a liner received by the frame, in accordance with features of the present invention.
Figure 7:
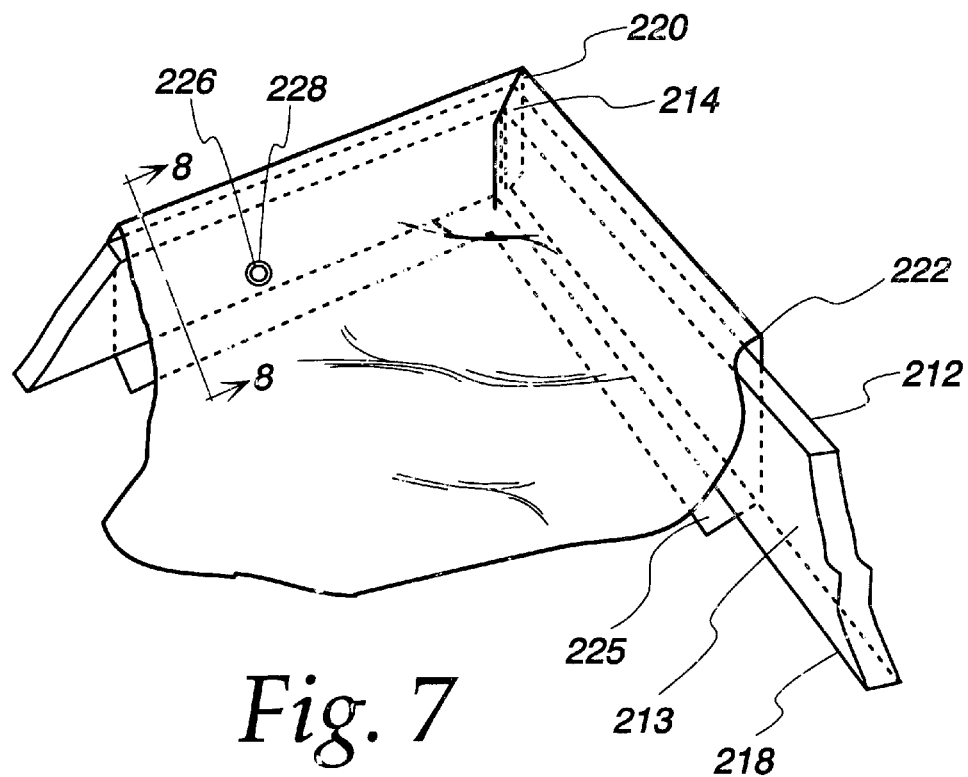
FIG. 7 is a view of FIG. 6 along lines 7—7.

FIGS. 6 and 7 are partial cutaway views of a corner of the device, with the liner 222 encapsulating the frame 212. This encapsulation isolates the frame 212 from any fluids contacting the liner 222. The liner 222 is constructed so that its corners 220 are form fitted to the corners 214, 215 of the frame. A depending portion of the liner 222 terminates with an inwardly directed tongue 225. The tongue 225 serves to substantially encapsulate a downwardly facing surface 218 of the frame. The tongue also provides a means for removably attaching the liner 222 to the frame 212. Optionally, the tongue 225 can further define an upwardly directed portion (not shown) of the liner so as to facilitate contact of an inside surface 213 of the frame with the liner 222.

Figure 8:
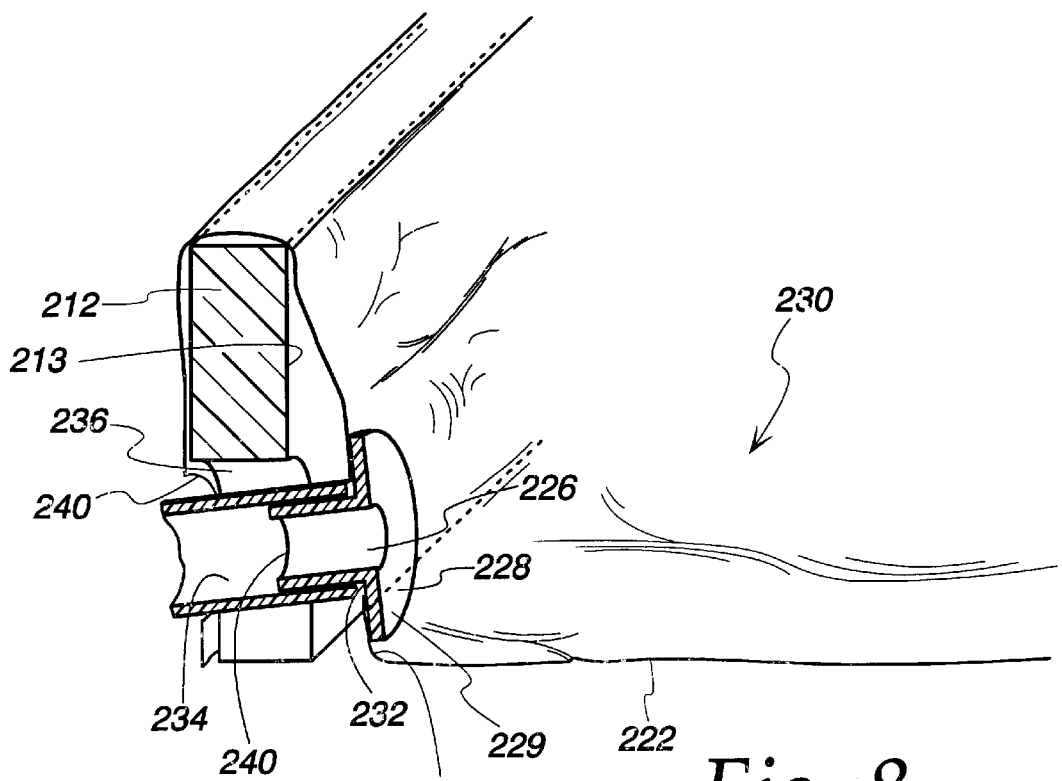
FIG. 8 is a view of FIG. 7 along lines 8—8.

The device further provides a means for evacuating fluid from a basin 230 which forms when the liner 222 is received by the frame 212. As depicted in FIG. 8, the evacuation means comprises a region of the liner forming an aperture 226, the periphery of which is attached to a fitting 228. The fitting 228 defines a neck or similar protuberance 232 adapted to removably receive a first end of a conduit 234. A second end of the conduit (not shown) is directed to either a drain, or a fluid storage container. The protuberance 232 receives the conduit in a male-female configuration and hold the conduit in place via friction or in a threaded fashion.

The fitting 228 is attached to the liner 222 via adhesive, rf welding, or other suitable type of method for providing a hermetic seal between the liner and the fitting. Preferably, the fitting and liner become integrally molded.

Unlike the connection relationship between the liner and the fitting, the fitting and evacuation conduit 234 are removably attached to each other, with the conduit slidably received by the fitting, or the conduit mating with the fitting in a male-female threaded configuration.

To accommodate extension of the conduit from the device, a region of the frame 212 adjacent the evacuation means defines a notch 236 or aperture through which the conduit 234 can extend. Similarly, a depending portion 240 of the liner 222 also defines a notch 240 or aperture, through which the conduit can extend.

The notch 236 in the frame as depicted in FIG. 8 provides a means for more efficient fluid evacuation from the basin. Specifically, the notch allows for downward movement of the fitting 228 when the unit is assembled and in use. This feature facilitates more efficient drainage of any fluids residing in the basin 230, particularly when the conduit 234 is weighted down at its other end by an ever-filling reservoir.

Another means for providing efficient evacuation of fluid through the conduit includes a fitting with a flexible (i.e., reversibly deflectable) protuberance 232. One type of deflectable protuberance is of an articulated configuration, or else constructed of reversibly deformable material. Such a configuration serves to isolate movement of the fitting 228 to its neck or protuberance region 232 so that an inwardly-facing surface 229 of the fitting that is in fluid communication with the basin remains relatively stationary. Fittings with such articulated regions are available from a myriad of commercial suppliers, including Consolidated Plastics, of Houston, Tex., and Corky-Roberts of Florida.

To further expedite evacuation of fluid from the basin 230, the fitting 228 is situated at a corner 231 of the liner 222 formed by the junction point of an upwardly extending portion of the liner and a generally horizontal, medially extending portion of the liner. Alternatively, the fitting 228 is situated on the horizontally extending portion of the liner 222. In this last instance, the device is positioned on a support surface (not shown) so that any weight from fluid in the basin 230 or from a patient does not occlude the conduit during drainage. One position would be for the device to partially protrude off the support surface so that the drainage conduit would be free-hanging and not otherwise hampered from the weight of the basin's contents.

Figure 9:
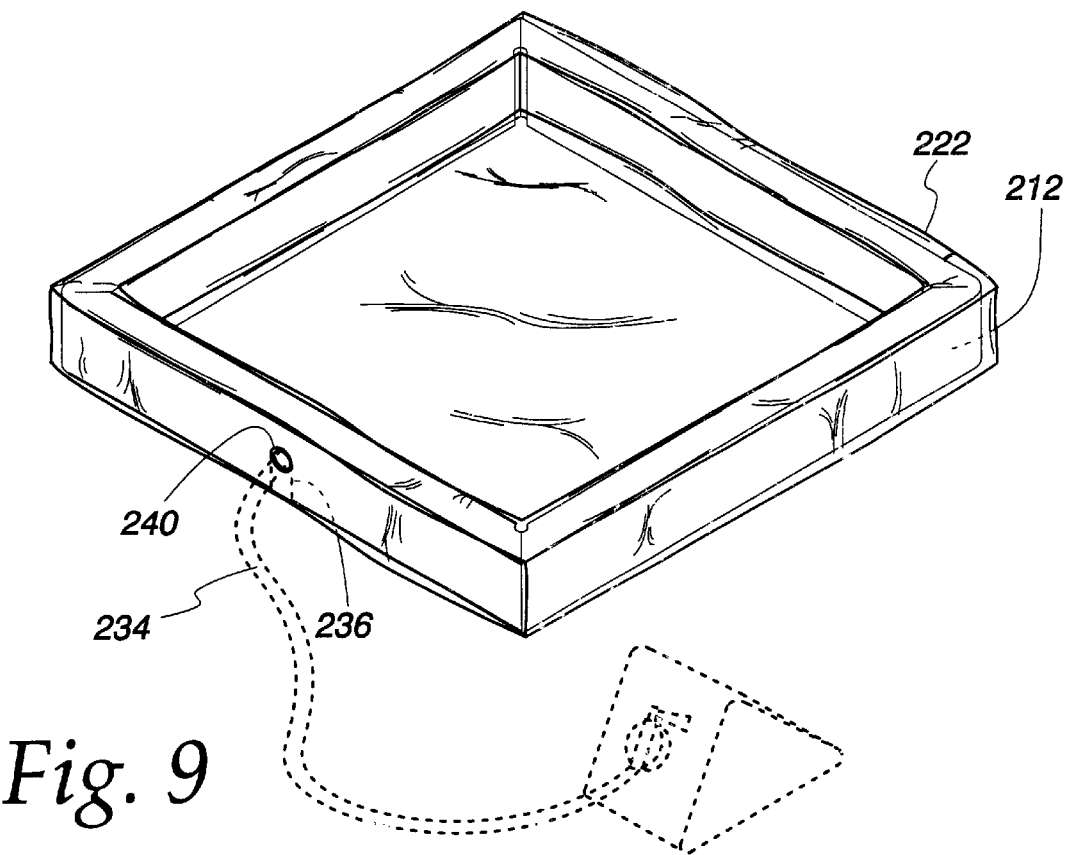
FIG. 9 is a view of an assembled decontamination device, in accordance with features of the present invention.
Figure 10:
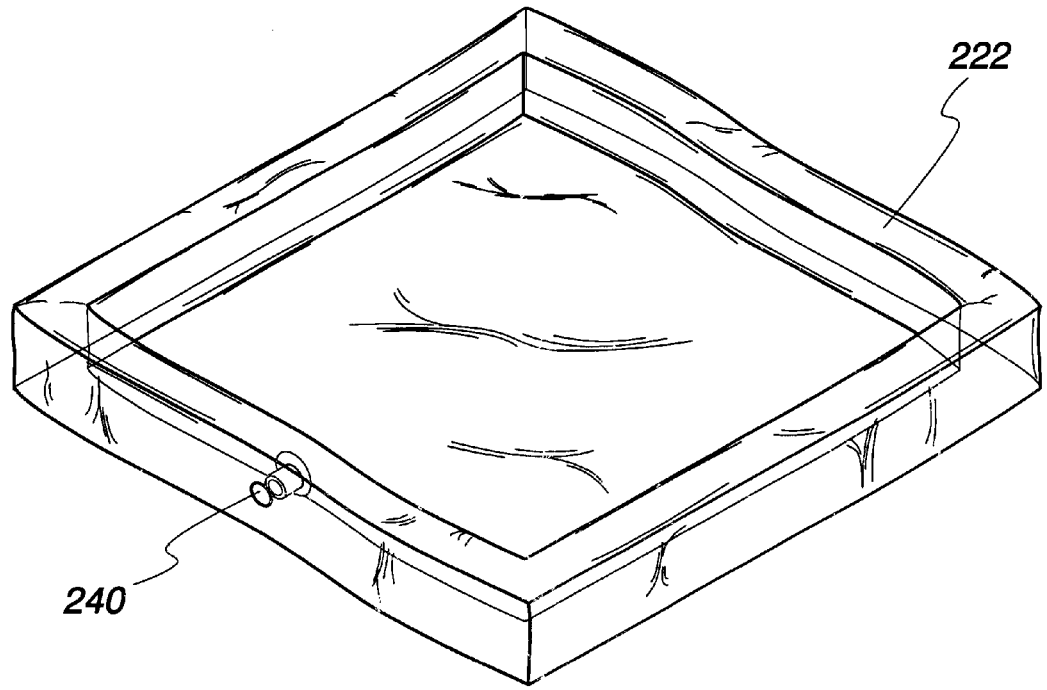
FIG. 10 is an exploded view of the assembled decontamination device, in accordance with features of the present invention.
Figure 10:
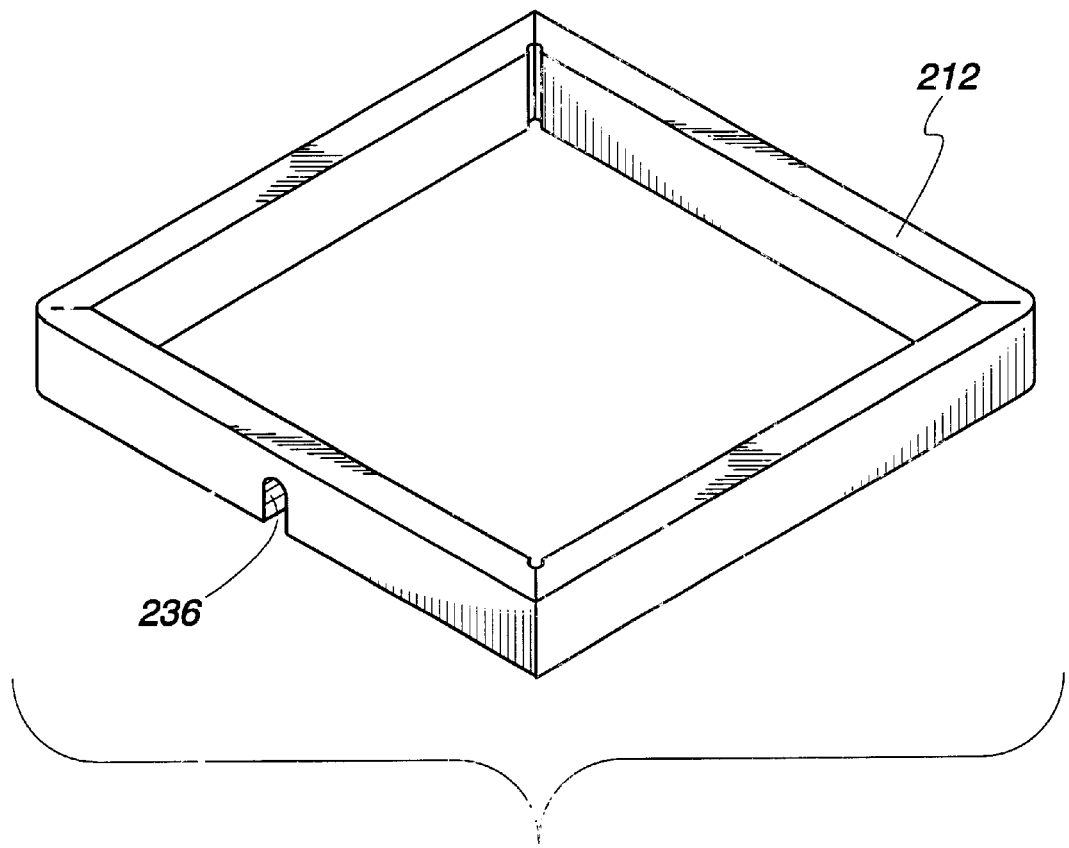

FIG. 9 shows a view of the invented decontamination device when it is fully assembled together with an optional waste container attached thereto. As can be noted in FIG. 9, the notch 236 in the 10 is an exploded view of FIG. 9 showing how the liner 222 fits over the frame 212.

It should be noted that the embodiment as illustrated in FIGS. 5–10 optionally can include the cushioning means 64 heretofore depicted in FIGS. 1–4.

Material Detail

A myriad different materials are suitable for the flexible membranes 44, 74, 100, and 222, the frame members 48 and 52, the support cushion 64, and the drainage conduit 30 and receptacle 34. The frame and supporting means comprise reversibly deformable materials allowing for the support of the body region over a wide area. The deformable materials typically are covered with a chemically-resistant material. The main consideration is that the materials be light and chemically resistant. The materials disclosed in U.S. Pat. No. 5,568,817 for the frame of the whole-body contamination device can be used for the frame of the present invention and for the cushion 64. Generally, suitable frame materials include, but are not limited to, plastic, glass, fiberglass, ceramics, wood, cardboard, polyvinyl chloride, thermoplastics, polyesters, closed cell foam such as ethyl vinyl acetate, and Cor-X™. Reversibly deformable materials are preferable.

For the membranes 44, 74, 100 and 222, the impermeable materials disclosed in U.S. Pat. No. 5,568,817 for use in the manufacture of a liner for a whole-body contamination device are appropriate here as well. Generally, suitable membrane materials include, but are not limited to, fluoroplastics, polyvinyl chloride, polyurethane, polyethylene, and polypropylene. The membranes' thickness should be around 5 to 10 mils (one mil=0.001 in).

The present invention is applicable to a multitude of fields beyond medical decontamination. For instance, it can be used for veterinary medicine, the handling of a leaking canister or conduit, the performance of a field chemistry test, and the like. Also, and as noted supra, the device can be used as a surgical or suture tray. In this regard, an absorbent material can replace the supporting means 64. This absorbent material can be isolated in one region of the inside bottom surface of the basin 41, 78 or cover the entire inside bottom surface.

While the invention has been described with reference to details of the illustrated embodiments, these details are not intended to limit the scope of the invention as defined in the appended claims.

What is claimed is:

1. A containing device for fluids emanating from a portion of a patient's body comprising:

a frame comprised of a reversibly deformable material;

a membrane for containing the fluids emanating from the portion of the patient's body;

means for attaching said membrane to said frame; and means for collapsing said frame for storage, said collapsing means further comprising mitered corners that allow for collapsing said frame along an axis defined by two points located at diametrically opposed corners.

2. The device as recited in claim 1 wherein a liner prevents the frame from collapsing.

3. The device as recited in claim 2 wherein said frame can be deployed in a time as short as five seconds.

4. The device as recited in claim 1 further comprising means positioned within said basin for supporting the body region.

5. The device as recited in claim 1 wherein the membrane is impervious to liquid.

6. The device as recited in claim 1 wherein said positioning means includes opposing frame sides having niches adapted to accommodate the transverse positioning the portion of the patient's body.

7. The device as recited in claim 1 wherein said reversibly deformable material is capable of preventing fluid leakage between the body portion and said frame.

8. The device as recited in claim 7 wherein said preventing means includes a niche configuration adapted to mate with the body portion.

9. A device for containing bodily fluids emanating from an isolated portion of a patient's body comprising:

a frame comprised of a reversibly deformable material;

a membrane cooperatively engaging said frame so as to contain the bodily fluids emanating from the isolated portion of the patient's body;

means for collapsing said frame for storage; and means for draining the fluid from the basin, said draining means including a notch in said frame to allow for downward positioning of a drain fitting.

10. The device as recited in claim 9 wherein the draining means directs the fluid to a container.

11. The device as recited in claim 10 wherein the container is removably attached to the draining means.

12. The device as recited in claim 9 wherein said draining means includes means for lowering a portion of said frame.

13. A method for containing bodily fluids emanating from a person, said method comprising the steps of:

a) providing a frame comprised of a reversibly deformable material;

b) providing a membrane capable of cooperatively engaging said frame so as to contain the bodily fluids emanating from the person's body;

c) positioning the portion of the person's body having fluids emanating therefrom so as to promote the collection of the bodily fluids by said membrane; and;

d) collapsing said frame for storage, said collapsing step including the step of providing mitered corners that allow for collapsing said frame along an axis defined by two points located at diametrically opposed corners.

* * * * *